United States Patent

Okano et al.

Patent Number: 5,948,421
Date of Patent: Sep. 7, 1999

[54] AQUEOUS LIQUID AGRICULTURAL COMPOSITION

[75] Inventors: Tetsuya Okano; Keiko Hasebe; Tadayuki Suzuki; Yuichi Hioki; Keiichiro Tomioka, all of Wakayama; Tatsuo Sato, Ibaraki, all of Japan

[73] Assignees: Kao Corporation, Tokyo, Japan; Monsanto Company, St. Louis, Mo.

[21] Appl. No.: 08/945,520

[22] PCT Filed: Mar. 5, 1997

[86] PCT No.: PCT/JP97/00667

§ 371 Date: Oct. 29, 1997

§ 102(e) Date: Oct. 29, 1997

[87] PCT Pub. No.: WO97/32476

PCT Pub. Date: Sep. 12, 1997

[30] Foreign Application Priority Data

Mar. 6, 1996 [JP] Japan ................................. 8-049319

[51] Int. Cl.$^6$ .................................................. A01N 25/02
[52] U.S. Cl. .................... 424/405; 424/406; 514/114; 514/937; 514/971; 514/975; 504/206
[58] Field of Search ...................... 424/405, 406; 504/206, 116, 127, 187–189, 194; 514/971, 975, 937, 114

[56] References Cited

FOREIGN PATENT DOCUMENTS

| 0 509346-A1 | 10/1992 | European Pat. Off. |
| WO 95 17817 | 7/1995 | WIPO |
| WO 95 33379 | 12/1995 | WIPO |

Primary Examiner—Neil S. Levy
Attorney, Agent, or Firm—Birch, Stewart, Kolasch & Birch, LLP

[57] ABSTRACT

An aqueous liquid agricultural composition which is excellent in liquid stability even when it contains an agricultural chemical at a high concentration comprises (a) a water-soluble agricultural chemical, (b) at least one member selected from the group consisting of compounds represented by the following formula (I) and derivatives thereof, and (c) at least one member selected from the group consisting of salts of compounds represented by the following formula (II) with acids and compounds represented by the following formula (III):

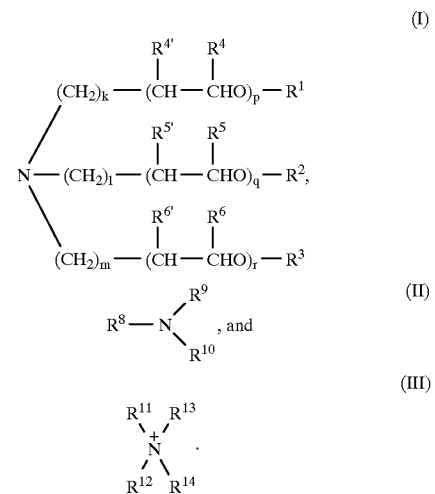

10 Claims, No Drawings

AQUEOUS LIQUID AGRICULTURAL COMPOSITION

BACKGROUND OF THE INVENTION

1. Field of the Invention

The present invention relates to a novel aqueous liquid agricultural composition and a novel adjuvant composition for agricultural chemicals.

2. Description of the Related Art

Agricultural chemicals including insecticides, fungicides (or bactericides), herbicides, miticides (or acaricides) and plant growth regulators have been used in various dosage forms, and one example thereof includes a liquid formulation comprising a water-soluble agricultural chemical. In such a liquid formulation, it is desirable that the concentration of the agricultural chemical is as high as possible. However, it is difficult to say that the concentrations of the agricultural chemicals of the liquid agricultural chemical formulations which are now commercially available are satisfactorily high.

Further, it has been known that the effects of agricultural chemicals can be enhanced by using cationic surfactants of an alkylene-oxide-addition type together with the agricultural chemicals (see WO95/33379). However, when liquid agricultural chemical formulations each comprising an agricultural chemical and the above-described cationic surfactant at high concentrations have been prepared, phase separation, sedimentaion of insoluble matters or the like has occurred in some cases. That is, it has been difficult to prepare a liquid agricultural chemical formulation which is uniform and stable. Particularly when the liquid formulation further comprises a chelating agent or a water-soluble inorganic salt, phase separation or sedimentaion of insoluble matters has readily occured.

DISCLOSURE OF THE INVENTION

SUMMARY OF THE INVENTION

An object of the present invention is to provide an aqueous liquid agricultural composition which contains an agricultural chemical at a high concentration and is excellent in stability.

Another object of the present invention is to provide a method for converting a certain agricultural composition into a stable liquid.

Still another object of the present invention is to provide an adjuvant composition for agricultural chemicals which is useful in the preparation of an aqueous liquid agricultural composition.

The present inventors have extensively studied to attain the above-mentioned objects. As a result of the studies, the present inventors have found that an aqueous liquid agricultural composition which contains an agricultural chemical at a high concentration and which is excellent in stability, can be prepared by using an agricultural chemical, a specific alkylene-oxide-addition-type surfactant having the excellent effect of enhancing the efficacy of the agricultural chemical, and at least one member selected from the group consisting of specific acid salts of amines and specific quaternary ammonium salts. Further, the present inventors have found that even when such the agricultural composition further contains a chelating agent or a water-soluble inorganic salt, the stability thereof can also be retained. The present invention has been completed on the basis of these findings.

Thus, the first embodiment of the present invention relates to an aqueous liquid agricultural composition comprising (a) a water-soluble agricultural chemical, (b) at least one member selected from the group consisting of compounds represented by the following formula (I) and derivatives thereof, and (c) at least one member selected from the group consisting of acid salts of compounds represented by the following formula (II) and compounds represented by the following formula (III):

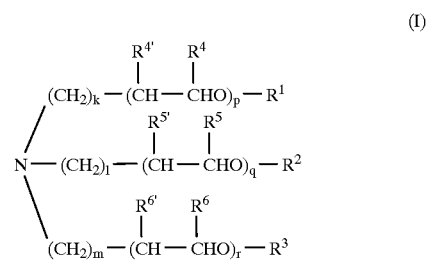
(I)

wherein $R^1$, $R^2$ and $R^3$ may be the same or different from one another and each independently represents a hydrogen atom, a linear or branched alkyl or alkenyl group having 5 to 29 carbon atoms, a group represented by the formula:

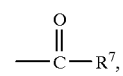

wherein $R^7$ represents a linear or branched alkyl or alkenyl group having 5 to 29 carbon atoms, or a group represented by the formula:

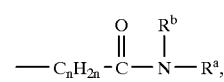

wherein $R^a$ represents a linear or branched alkyl or alkenyl group having 5 to 29 carbon atoms, $R^b$ represents a hydrogen atom, a linear or branched alkyl group having 1 to 30 carbon atoms or a linear or branched alkenyl group having 2 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30;

$R^4$ and $R^{4'}$ are both hydrogen atoms or one of them is a hydrogen atom and the other is a methyl group or an ethyl group, with the proviso that when two or more groups each represented by the formula:

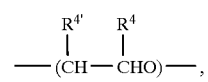

wherein $R^4$ and $R^{4'}$ are each as defined above, are contained therein, these groups may be the same or different from one another;

$R^5$ and $R^{5'}$ are both hydrogen atoms or one of them is a hydrogen atom and the other is a methyl group or an ethyl group, with the proviso that when two or more groups each represented by the formula:

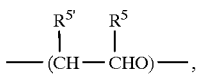

wherein $R^5$ and $R^{5'}$ are each as defined above, are contained therein, these groups may be the same or different from one another;

$R^6$ and $R^{6'}$ are both hydrogen atoms or one of them is a hydrogen atom and the other is a methyl group or an ethyl group, with the proviso that when two or more groups each represented by the formula:

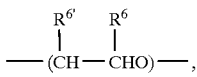

wherein $R^6$ and $R^{6'}$ are each as defined above, are contained therein, these groups may be the same or different from one another; and k, l and m may be the same or different from one another and are each independently a number of 0 to 6,

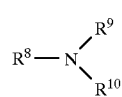

(II)

wherein, $R^8$ represents a linear or branched, or cyclic, alkyl or alkenyl group having 4 to 18 carbon atoms; and $R^9$ and $R^{10}$ may be the same or different from each other and are each independently a hydrogen atom, a methyl group or an ethyl group, and

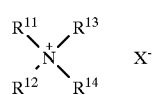

(III)

wherein $R^{11}$ represents a linear or branched alkyl or alkenyl group having 4 to 18 carbon atoms; $R^{12}$ represents a linear or branched alkyl group having 1 to 18 carbon atoms or a linear or branched alkenyl group having 2 to 18 carbon atoms; $R^{13}$ and $R^{14}$ may be the same or different from each other and are each independently a methyl group, an ethyl group or a benzyl group; and $X^-$ is a counter anion.

The agricultural composition of the present invention is in the form of "aqueous liquid". The term "aqueous liquid" herein means to aqueous fluid. More specially, the concept of the "aqueous liquid" in the present invention includes not only transparent aqueous solutions but also, e.g., emulsions and turbid ones, as long as separation and sedimentation are not observed and fluidity is retained. Accordingly, the agricultural chemical composition of the present invention contains water.

The aqueous liquid agricultural composition of the present invention further comprises, preferably, at least one member selected from the group consisting of chelating agents and water-soluble inorganic salts.

In the aqueous liquid agricultural composition of the present invention, component (a) is preferably a herbicide.

In the aqueous liquid agricultural composition of the present invention, component (b) is preferably at least one member selected from the group consisting of derivatives which are prepared by quaternizing the compounds represented by the above formula (I).

Usually, in the aqueous liquid agricultural composition of the present invention, component (c) is preferably at least one member selected from the group consisting of salts of the compounds represented by the above formula (II) with acids.

When the aqueous liquid agricultural composition of the present invention further comprises at least one member selected from the group consisting of chelating agents and water-soluble inorganic salts, component (c) is preferably at least one member selected from the group consisting of the compounds represented by the above formula (III).

In the aqueous liquid agricultural composition of the present invention, the weight ratio of component (b) to componet (c) [(b)/(c)] is preferably 9/1 to 1/9.

The aqueous liquid agricultural composition of the present invention contains effective amounts of components (a), (b) and (c).

Further, the second embodiment of the present invention relates a method for converting a composition (1) comprising (a) a water-soluble agricultural chemical and (b) at least one member selected from the group consisting of the compounds represented by the above formula (I) and derivatives thereof into a stable liquid, which comprises adding (c) at least one member selected from the group consisting of salts of the compounds represented by the above formula (II) with acids and the compounds represented by the above formula (III) to the composition (1).

The composition (1) may further comprise at least one member selected from the group consisting of chelating agents and water-soluble inorganic salts.

Furthermore, the third embodiment of the present invention relates an adjuvant composition for agricultural chemicals comprising (b) at least one member selected from the group consisting of the compounds represented by the above formula (I) and derivatives thereof, and (c) at least one member selected from the group consisting of salts of the compounds represented by the above formula (II) with acids and the compounds represented by the above formula (III).

The adjuvant composition for agricultural chemicals of the present invention may further comprise at least one member selected from the group consisting of chelating agents and water-soluble inorganic salts.

Further scope and applicability of the present invention will become apparent from the detailed description and examples given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description and these examples.

DETAILED DESCRIPTION OF THE INVENTION

First, each component of the present invention will be illustrated.

Component (a)

The term, "an agricultural chemical" to be used in this description and claims refers a compound which is used as an active component in usual agricultural compositions or agricultural preparations. Examples thereof include a fungicide (or a bactericide), an insecticide, a miticide (or an acaricide), a herbicide and a plant growth regulator.

The agricultural chemical to be used in the present invention is water-soluble. "Water-soluble" means that its solubility in water at 25° C. is 5% or above. Further, agricultural chemicals of which the formulations are generally marketed in the form of a liquid formulation [see Noyaku Handobukku (Agricultural Chemical Handbook) 1994, published by Nippon Shokubutsu Boeki Kyokai)] are also included in the scope of the water-soluble agricultural chemicals of the present invention.

Next, specific examples of the water-soluble agricultural chemicals to be used in the agricultural composition of the present invention will be cited, though the water-soluble agricultural chemicals in the present invention are not restricted thereto.

Examples of fungicides include Ambam [diammonium ethylenebis(dithiocarbamate)], Thiabendazole [2-(4-thiazolyl)benzoimidazole], Iminoctadine acetate [1,1'-iminiodi(octamethylene)diguanidium triacetate], Dimethylmol (5-butyl-2-dimethylamino-6-methylpyrimidin-4-ol), Propamocarb hydrochloride [propyl 3-(dimethylamino) propylcarbamate hydrochloride] and Hydroxyisoxazole (3-hydroxy-5-methylisoxazole).

Examples of herbicides include dipyridyl herbicides, diazine herbicides, benzoic acid herbicides, phenoxy herbicides, organophosphorus herbicides and aliphatic herbicides. Specific examples of the dipyridyl herbicides include Paraquat (1,1'-dimethyl-4,4'-bipyridinium dichloride) and Diquat (6,7-dihydrodipyrido[1,2-a:2',1'-c]-pyrazinediium dibromide). Specific examples of the diazine herbicides include Bentazon (3-isopropyl-3H-2,1,3-benzothiadiazin-4-one-2,2-dioxide) and salts thereof (e.g., its sodium salt). Specific examples of the benzoic acid herbicides include MDBA (dicamba) (3,6-dichloro-2-methoxybenzoic acid dimethylamine salt) and Imazapyr [isopropylammonium (RS)-2-(4-isopropyl-4-methyl-5-oxo-2-imidazolin-2-yl)nicotinate]. Specific examples of the phenoxy herbicides include 2,4-D sodium salt (sodium 2,4-dichlorophenoxyacetate), MCP (2-methyl-4-chlorophenoxyacetic acid) and salts thereof (e.g., its sodium salt), MCPP [d,1-2-(4-chloro-o-tolyloxy)propionic acid] and salts thereof (e.g., its potassium salt), and Triclopyr (3,5,6-trichloro-2-pyridyloxyacetic acid) and salts thereof (e.g., its triethylamine salt). Specific examples of the organophosphorus herbicides include Glyphosate [N-(phosphonomethyl)glycine] and water-soluble salts thereof, Bialophos [sodium salt of L-2-amino-4-[(hydroxy)(methyl) phosphinoyl]-butyryl-L-alanyl-L-alanine] and Glufosinate [ammonium DL-homoalanin-4-yl(methyl)phosphinate]. Further, a specific example of the aliphatic herbicides includes Tetrapione (sodium 2,2,3,3-tetrafuluoropropionate).

Furthermore, examples of plant growth regulators include MH (maleic hydrazide), Ethrel (2-chloroethylphosphonic acid), UASTA and Bialophos.

Herbicides are preferred as the agricultural chemicals to be used in the agricultural composition of the present invention. Among the herbicides described above, organophosphorus herbicides, in particular, Glyphosate [N-(phosphonomethyl)glycine] and water-soluble salts thereof, Bialophos [sodium salt of L-2-amino-4-[(hydroxy)(methyl)-phosphinoyl]butyryl-L-alanyl-L-alanine] and Glufosinate [ammonium DL-homoalanin-4-yl(methyl)phosphinate] are preferred.

Component (b)

The agricultural composition, and the adjuvant composition for agricultural chemicals of the present invention contain the compound represented by the above general formula (I) or the derivative thereof. Such a compound or a derivative thereof exerts the excellent effect of enhancing the efficacy of the agricultural chemical.

The compound of formula (I) according to the present invention can be synthesized, for example, as follows, when it is an ester type. First, a fatty acid is reacted with a trialkanolamine to esterify. Subsequently, an alkylene oxide is added to the resulting ester. Alternatively, into a mixture containing a suitable fat or oil and a trialkanolamine at an arbitrary ratio, an alkylene oxide is introduced while stirring. Thus, the addition reaction with an alkylene oxide may be effected while effecting transesterification. In this reaction, the number of the acyl group per an amine skeleton, that is the proportion of esterification, can be desirably controlled by suitably selecting the ratio of the fat or oil to the trialkanolamine.

Further, those of an alkyl ether type among the compounds represented by formula (I) can be synthesized, for example, as follows. First, an alkylene oxide is added to an alcohol such as dodecanol to be an adduct of an alcohol with an alkylene oxide. Next, halogenation of the adduct with, e.g., hydrochloric acid is effected to substitute a halogen atom for hydrogen atom which is present at the terminal hydroxyl group of the adduct. Subsequently, the resulting reaction product is reacted with an organic amine such as ethanolamine to thereby aminating the halogenated terminal thereof. An alkylene oxide is further added to the resulting reaction product, according to necessity.

Furthermore, those of a monoalkylamide ether type among the compounds represented by formula (I) can be synthesized, for example, as follows. First, an alkylene oxide is added to an alkanolamine such as triisopropanolamine to be an adduct of an alkanolamine with an alkylene oxide. Next, the adduct is reacted with, e.g., sodium monochloroacetate to be a carboxy-methylated derivative of the adduct. Subsequently, the resulting reaction product is reacted with an organic amine such as octadecylamine to thereby convert the carboxyl group thereof to an amide group.

Of course, the processes for producing the compound of formula (I) according to the present invention are not restricted to those described above.

Examples of the derivatives of the compounds represented by formula (I) include salts of the compounds with acids, and quaternized products of the compounds (i.e., quaternary ammonium salts). Specific examples of the salts of the compounds with acids include salts of the compounds with inorganic acids (e.g., hydrochlorides, sulfates and phosphates) and those of the compounds with organic acid (e.g., acetates), while specific examples of the quaternized products include those quaternized with methylchloride, dimethylsulfuric acid, diethylsulfuric acid, benzylchloride and the like.

Among the compounds of formula (I) according to the present invention, compounds represented by formula (1) wherein all of $R^4$, $R^{4'}$, $R^5$, $R^{5'}$, $R^6$ and $R^{6'}$ are hydrogen atoms, and another compounds represented by formula (1) wherein the combinations of $R^4$ and $R^{4'}$, those of $R^5$ and $R^{5'}$, and those of $R^6$ and $R^{6'}$ are each a combination of a hydrogen atom with a methyl group are preferable. Further, $R^1$ and $R^7$ in formula (I) are each preferably a linear or branched alkyl or alkenyl group having 7 to 25 carbon atoms, particularly 7 to 21 carbon atoms. Furthermore, p, q and r in formula (1) may be the same or different from one another and are each independently, preferably a number of 1 to 20 on the average, and still more preferably a number of 1 to 10.

Component (c)

The agricultural composition of the present invention further comprises (c) at least one member selected from the group consisting of salts of the compounds represented by the above formula (II) with acids and the compounds represented by the above formula (III), in addition to components (a) and (b) described above. Further, the adjuvant composition for agricultural chemicals of the present invention also comprises component (c). By using such the salt or such the compound [i.e., component (c)], the content of the agricultural chemical can be enhanced.

In formula (II), $R^8$ is preferably an alkyl or alkenyl group having 6 to 18, particularly 6 to 14, carbon atoms, or preferably a cyclohexyl group. While, $R^9$ and $R^{10}$ are each preferably a hydrogen atom or a methyl group.

In the present invention, the amine compound represented by formula (II) is used in the form of a salt thereof with an acid, in view of handling thereof. Such the salt can be prepared by treating the amine compound represented by formula (II) with an inorganic acid such as hydrochloric acid, sulfuric acid, nitric acid and phosphoric acid, or an organic acid such as acetic acid, alkyl phosphates and polyoxyalkylene alkyl ether phosphates.

While, in the above formula (III), $R^{11}$ is preferably an alkyl or alkenyl group having 6 to 18 carbon atoms, and $R^{12}$ is preferably a methyl group or an alkyl or alkenyl group having 6 to 18 carbon atoms. Further, it is particularly preferable that $R^{13}$ and $R^{14}$ are each a methyl group.

Examples of the counter ions, $X^-$, in formula (III) include halide anions such as $Cl^-$, $Br^-$ and $I^-$, alkylsulfate anions, fatty acid anions, alkylphosphate anions and polyoxyalkylene alkyl ether phosphate anions.

The aqueous liquid agricultural composition of the present invention comprises the above-mentioned components (a), (b) and (c). This agricultural composition usually contains water as well, and can be prepared by, for example, dissolving components (a), (b) and (c) in water. Although the amounts of components (a), (b) and (c) and water in the aqueous liquid agricultural composition according to the present invention are not particularly restricted, it is preferable that they are used in the amounts as described below, based on the entire weight of the composition:

Component (a): preferably 25 to 85% by weight, still more preferably 35 to 65% by weight, Component (b): preferably 0.35 to 30% by weight, still more preferably 0.7 to 20% by weight, Component (c): such an amount that the weight ratio, (b)/(c), is in the range of preferably 9/1 to 1/9, still more preferably 8/2 to 2/8, and Water: the balance.

Thus, according to the present invention, it is possible to elevate the concentration of component (a), i.e., the agricultural chemical, as compared with those of the conventional liquid agricultural compositions. Further, even when the agricultural composition contains also a chelating agent and/or a water-soluble inorganic acid, it is possible to elevate the concentration of the agricultural chemical, and the concentration(s) of the chelating agent and/or the water-soluble inorganic acid, as compared with those of the conventional liquid agricultural compositions. Even when the aqueous liquid agricultural composition of the present invention contains the above-mentioned agricultural chemical and others at such the high concentrations, the composition is stable. However, the concept of the aqueous liquid agricultural composition according to the present invention also includes agricultural compositions having a low concentration of the agricultural chemical which can be applied as such to the crops.

The agricultural composition of the present invention may further comprise a surfactant other than components (b) and (c). Examples of the surfactants capable of being used with components (b) and (c) include nonionic surfactants.

Specific examples of the nonionic surfactants include polyoxyethylene alkyl ethers, polyoxyethylene alkyl aryl ethers, condensates of polyoxyethylene alkyl aryl ethers and formaldehyde, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, esters of polyoxyalkylene block copolymers and alkyl glycerols, polyoxyalkylene alkyl sulfonamides, polyoxyalkylene rosin esters, polyoxypropylene block copolymers, polyoxyethylene oleyl ethers, polyoxyalkylene alkyl phenols, alkyl glycosides, alkyl polyglycosides and polyoxyalkylene alkyl polyglycosides, and one of them or a mixture of two or more of them is used in the present invention.

When these nonionic surfactants are also used, the amount thereof is such that the weight ratio of component (b) to the nonionic surfactant is in the range of preferably from 9.1/0.9 to 0.9/9.1, and still more preferably from 8.0/2.0 to 2.0/8.0.

The agricultural composition of the present invention may comprise also at least one member selected from the group consisting of chelating agents and water-soluble inorganic salts at need, as long as the stability thereof is not deteriorated thereby. When the agricultural composition of the present invention comprises also at least one member selected from the group consisting of chelating agents and water-soluble inorganic salts, the efficacy of the agricultural chemical can be further enhanced.

Examples of inorganic salts include inorganic ammonium salts such as ammonium sulfate, ammonium nitrate, ammonium phosphate, ammonium thiocyanate, ammonium chloride and ammonium sulfamate; potassium dihydrogenphosphate; dipotassium hydrogenphosphate; sodium dihydrogenphosphate; disodium hydrogenphosphate; and sodium carbonate; among which inorganic ammonium salts are preferred.

The water-soluble inorganic acid is used in an amount of preferably 2 to 25% by weight, still more preferably 5 to 20% by weight, based on the entire weight of the agricultural composition of the present invention.

The chelating agent to be used in the present invention is not particularly limited, as long as it has the ability to chelate a metal ion.

Examples of the chelating agents to be used in the agricultural composition of the present invention include those based on aminopolycarboxylic acids, aromatic and aliphatic carboxylic acids, amino acids, ether polycarboxylic acids, phosphonic acids such as iminodimethylphosphonic acids (IDP) and alkyldiphosphonic acids (ADPA), and hydroxycarboxylic acids; polyelectrolytes (including oligoelectrolytes); and dimethylglyoxime (DG). These chelating agents may be each as such, i.e., in the form of a free acid, or in the form of a salt such as a sodium salt, a potassium salt and an ammonium salt. Alternatively, it may take a form of an ester derivative thereof which can be hydrolyzed.

Specific examples of the aminopolycarboxylic acid chelating agent include:

a) compounds represented by the formula: $RNY_2$, b) compounds represented by the formula: $NY_3$, c) compounds represented by the formula:

d) compounds represented by the formula: R—NY—$CH_2CH_2$—$NY_2$, e) compounds represented by the formula: $Y_2N-R'-NY_2$, and f) compounds which are similar to compounds (e) and each has more than four Y's, for example, a compound represented by the formula:

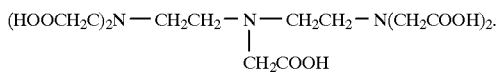

In the above formulas, Y represents $-CH_2COOH$ or $-CH_2CH_2COOH$; R represents any group constituting known chelating agents of this type, for example, a hydrogen atom, an alkyl group, a hydroxyl group or a hydroxyalkyl group; and R' represents any group constituting known chelating agents of this type, for example, an alkylene group or a cycloalkylene group.

Representative examples of the aminopolycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl) ethylenediaminetriacetic acid (EDTA-OH) and glycol ether diaminetetraacetic acid (GEDTA), and salts thereof.

Examples of the aromatic and alipatic carboxylic acid chelating agents to be used in the present invention include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acids (including anthranilic acid), phthalic acid, trimellitic acid and gallic acid, and salts, methyl esters and ethyl esters thereof.

Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include diglycollic acid, compounds represented by the following formula, analogues of the compounds represented by the following formula and salts thereof (such as sodium salts thereof):

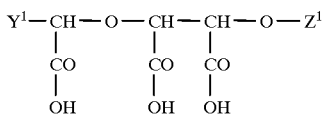

wherein $Y^1$ represents a hydrogen atom, $-CH_2COOH$ or $-COOH$; and $Z^1$ represents a hydrogen atom,

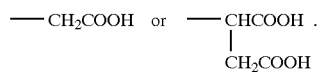

Examples of the hydroxy carboxylic acid chelating agents to be used in the present invention include malic acid, citric acid, glycollic acid, gluconic acid, heptonic acid, tartaric acid and lactic acid, and salts thereof.

Examples of the phosphoric acid chelating agents to be used in the present invention include orthophosphoric acid, pyrophosphoric acid, triphosphoric acid and polyphosphoric acids.

Examples of the polyelectrolytes (including oligoelectrolytes) to be used in the present invention include polyacrylic acid, polymaleic anhydride, α-hydroxyacrylic acid polymer, polyitaconic acid, copolymers comprising two or more of the monomers constituting these polymers, and epoxysuccinic acid polymer.

In addition, ascorbic acid, thioglycollic acid, phytic acid, glyoxylic acid and glyoxalic acid, and salts thereof may also be preferably used as a chelating agent in the present invention.

The agricultural composition of the present invention contains the chelating agent preferably in an amount of 0.05 to 15 moles per mole of component (b).

The agricultural composition of the present invention may further comprises a pH regulator and/or a thickener at need, as long as the stability thereof is not deteriorated thereby.

Examples of the pH regulators to be used in the present invention include citric acid, phosphoric acids (e.g., pyrophosphoric acid) and gluconic acid, and salts thereof.

Examples of the thickeners to be used in the present invention include natural, semi-synthetic and synthetic water-soluble thickeners. Specific examples of the natural mucilages usable as the natural thickeners include xanthan gum and Xanfloo derived from microorganisms, and pectin, acacia and guar gum derived from vegetables. Specific examples of the semisynthetic mucilages usable as the semisynthetic thickeners include methylated, carboxyalkylated and hydroxyalkylated celluloses, such as methylcellulose, carboxymethylcellulose and hydroxymethylcellulose; methylated, carboxyalkylated and hydroxyalkylated starch derivatives; and sorbitol. Further, specific examples of the synthetic mucilages usable as the synthetic thickeners include polyacrylates, polymaleates, polyvinylpyrrolidones and adducts of pentaerythritol with ethylene oxide.

The agricultural composition of the present invention may further comprise at least one member selected from the group consisting of plant growth regulators other than those described as the specific examples of the plant growth regulators in the illustration of component (a), fertilizers and preservatives.

The agricultural composition of the present invention is used after diluting with water or as such.

The agricultural chemical composition of the present invention is used in order to control fungi (or bacteria), insects, mites (or acarids) and herbs or to regulate the growth of plants.

The second embodiment of the present invention relates to a method for converting a composition (1) comprisining components (a) and (b) into a stable liquid, which comprises adding component (c) to the composition (1).

The concept of the stabilization of the composition (1) by adding component (c) thereto includes (i) a method comprising adding component (c) as one component of the desired composition to water together with other component (s) in the preparation of the desired composition, (ii) a method comprising preparing a desired composition by using a mixture of components (b) and (c) which has been preliminalily prepared, and (iii) a method comprising adding component (c) to the composition (1) which has been prepared.

By adding component (c), the stability of the composition (1) comprising components (a) and (b) is improved. The effect of improving the stability of a liquid by component (c) is satisfactorily exhibited even when a component such as water-soluble inorganic salts which deteriorates the stability of a liquid, e.g., a solution, is added to the composition. "The improvement of the stability of a liquid" herein means that, for example, the separation of a liquid to two or more layers (or phases) or the formation of sedimentation from a liquid can be prevented. Due to no occurrence of layer separation and sedimentation, a lot of advantages including, e.g., the prevention of separation and/or sedimentation during transportation of the agricultural composition, and the ease of dilution of the agricultural composition, can be brought about by the present invention.

The present invention provides as above shown an agricultural composition comprising (a), (b) and (c). It may further at least one selected from a chelating agent and an water-soluble inorganic salt. In addition the invention provides an adjuvant composition for agricultural chemicals comprising (b) and (c), preferably at a mixing weight ratio of 9/1 to 1/9. The adjuvant composition may further comprise at least one member selected from the group consisting of chelating agents and water-soluble inorganic salts, that is, a chelating agent and/or a water-soluble inorganic salt.

Each of the component (b), the chelating agent and the water-soluble inorganic salts can enhance the efficacies of agricultural chemicals. The component (c) works to improve stability of a system where a water-soluble agricultural chemical (a) and the component (b) and optionally a water-soluble inorganic salt and/or a chelating agent co-exist.

The form of the adjuvant composition for agricultural chemicals according to the present invention is not restricted, and the composition may be a liquid, a solid (e.g., a powder), a suspension or the like. The adjuvant composition for agricultural chemicals of the present invention may contain other additive(s) such as solvents, emulsifiers, dispersants and carriers, depending upon the formulation or form thereof.

The above-mentioned agricultural composition of the present invention, the dilution of the agricultural composition, and the liquid formulation containing an agricultural chemical and the active components of the adjuvant composition for agricultural chemicals according to the present invention are applied to plants, cereals, vegetables, fruits, trees, fruit trees, grasses, weeds and seeds, and, at the same time, fungi, bacteria, insects, mites and acarids, by a method such as spraying. In other words, they are applied to a locus shch as a farm, a field, a plantation, a fruit garden, an orchard, a flower garden, a lawn, a wood and a forest.

According to the present invention, an aqueous liquid agricultural chemical composition, which is excellent in liquid stability, particularly in liquid stability when the liquid suffers from tempearture changes, even though the liquid contains an agricultural chemical at a high concentration, can be obtained. Further, according to the method of the present invention, it becomes possible to prepare a stable, aqueous liquid agricultural chemical composition, even though the composition contains an agricultural chemical in a large amount. Furthermore, it becomes possible to prepare a stable, aqueous liquid agricultural composition which does not suffer from salting out, even though the composition contains an agricultural chemical and further at least one member selected from the group consisting of chelating agents and water-soluble inorganic salts. In addition, by using the adjuvant composition for agricultural chemicals of the present invention, the enhancement of the efficacy of an agricultural chemical and the stabilization of a liquid formulation containing an agricultural chemical and the active components of the adjuvant composition for agricultural chemicals according to the present invention, can be attained simultaneously.

EXAMPLES

The present invention will now be described in more detail by referring to the following Examples which should not be thought as limiting the scope of the present invention.

Example 1

Glyphosate acid (N-phosphonomethylglycine) was synthesized by a known method. Then, the Glyphosate acid was neutralized with each of isopropylamine and ammonia for converting it into a water-soluble salt thereof. By using Glyphosate salts thus prepared, commercially available glufosinate monoammonium salt, and components (b) and (c) which will be shown in Table 1, aqueous liquid agricultural (herbicide) compositions which will be shown in Tables 2 to 7 were prepared.

With respect to each of the aqueous liquid agricultural (herbicide) compositions thus prepared, the conditions (conditions at a room temperature immediately after the preparation) of the compositions were observed with the naked eye. Next, only the compositions, which were in the state of one solution and trasparent immediately after the preparation thereof, were subjected to a stability test. The stability test was effected by storing the compositions in a thermostatic chamber of $-5°$ C. or $60°$ C. for seven days, taking out the compositions from the thermostatic chamber, and observing the conditions of the compositions with the naked eye. Compositions not occuring phase separation, sedimentation and crystallization were judged as stable.

Tables 2 to 7 show the results.

As Tables 2 to 7 show, there is understood that the aqueous liquid agricultural (herbicide) compositions of the present invention are excellent in the conditions immediately after the preparation thereof, as compared with comparative products, and are also excellent in the stability in storage at a high temperature and a low temperature. On the other hand, since all of the comparative products were separated into 2 phases immediately after the preparation thereof, they could not be subjected to the stability test.

Further, weeding tests were effected in the following manner with the use of the aqueous liquid agricultural (herbicide) compositions of the present invention which will be shown in Tables 2 to 7, and commercial products.

First, by using Wagner's pots (diameter: 15 cm), crabgrass and cabbage were each grown by a universally known method. Among crabgrasses and cabbages grown, those, of which the growthes were each in a desired range (i.e., uniform), were selected. While, the aqueous liquid agricultural (herbicide) compositions of the present invention and, a Glyphosate herbicide and a Glufosinate herbicide which were commercial products were each diluted with water in such a manner that the concentration of the Glyphosate salt, calculated in terms of Glyphosate acid, and that of the Glufosinate salt, calculated in terms of Glufosinate acid would be each a definite one. The dilutions thus prepared were each applied to each of the crabgrasses and the cabbages which had been grown in Wagner's pots to evaluate the effects of weeding.

As a result, the aqueous liquid agricultural (herbicide) compositions of the present invention exhibited the effects of weeding comparable or superior to those of the commercial products.

Example 2

Components (b) and (c) which will be shown in Table 1, adjuvant compositions for water-soluble agricultural chemicals which will be shown in Tables 8 were prepared.

With respect to each composition prepared, the conditions, at a room temperature, just after the preparation action of the compositions were visually observed with the naked eye. Next, only the compositions, which had been in the state of one solution and transparent or clear just after the preparation, were subjected to a stability test. The stability test was effected by storing the compositions in a thermostatic chamber of −5° C. or 60° C. for seven days, taking out the compositions from the thermostatic chamber, and observing the conditions of the compositions with the naked eye. Compositions not having been involved in phase separation, precipitates and deposited crystals were judged as stable.

Table 8 show the results.

As Table 8 show, it is noted that the compositions of the present invention are excellent in the conditions after the preparation thereof and are also excellent in the stability in storage at a high temperature and a low temperature.

The adjuvant compositions obtained in Table 8 were mixed with water-soluble agricultural chemicals as follows:

Agricultural compositon 1

| | |
|---|---|
| Glyphosate.diammonium salt | 42 parts by weight |
| Invention product 13 | 10 parts by weight |
| water | 48 parts by weight |

Agricultural compositon 2

| | |
|---|---|
| Glyphosate.diammononium salt | 36 parts by weight |
| Invention product 14 | 27 parts by weight |
| water | 37 parts by weight |

Agricultural compositon 3

| | |
|---|---|
| Glyphosate.monoisopropylamine salt | 54 parts by weight |
| Invention product 15 | 13 parts by weight |
| water | 33 parts by weight |

Agricultural compositon 4

| | |
|---|---|
| Glufosinate.monoammonium salt | 43 parts by weight |
| Invention product 16 | 27 parts by weight |
| water | 30 parts by weight |

The conditions of the agricultural compositions 1 to 4 were all in the state of one solution and transparent immediately after the preparation thereof. Then the compositions were subjected to a stability test. The stability test was effected by storing the compositions in a thermostatic chamber of −5° C. or 60° C. for seven days, taking out the compositions from the thermostatic chamber, and observing the conditions of the compositions with the naked eye. As a result, all compositions not having been found to have phase separation, precipitates and deposited crystals were judged as stable.

TABLE 1

| Compd. No. | Structure | |
|---|---|---|
| Component (b) | | |
| (1) | $\mathrm{N} \begin{cases} (C_2H_4O)_pCOR \\ (C_2H_4O)_qCOR \\ (C_2H_4O)_rH \end{cases}$ | R: an alkyl having a composition of beef tallow $p + q + r = 10$ |
| (2) | $\mathrm{N} \begin{cases} (C_2H_4O)_pR \\ (C_2H_4O)_qH \\ (C_2H_4O)_rH \end{cases}$ | R: an alkyl having a composition of coconut oil $p + q + r = 5$ |
| (3) | $H_3C-\overset{+}{\mathrm{N}} \begin{cases} (C_2H_4O)_pCOR \\ (C_2H_4O)_qCOR \cdot CH_3SO_4^- \\ (C_2H_4O)_rH \end{cases}$ | R: an alkyl having a composition of palm oil $p + q + r = 3$ |
| (4) | $H_3C-\overset{+}{\mathrm{N}} \begin{cases} CH_2-(C_2H_4O)_pR \\ (C_2H_4O)_qH \quad \cdot Cl^- \\ (C_2H_4O)_rH \end{cases}$ | R: an alkyl having a composition of coconut oil $p + q + r = 3$ |
| Component (c) | | |
| (5) | R—NH$_2$.HCl | R: octyl |
| (6) | R—NH$_2$.CH$_3$COOH | R: an alkyl having a composition of coconut oil |
| (7) | $\begin{array}{c} R \diagdown \overset{+}{\phantom{N}} \diagup CH_3 \\ \phantom{R}N \cdot Cl^- \\ H_3C \diagup \diagdown CH_3 \end{array}$ | R: an alkyl having a compositon of coconut oil |

TABLE 2

|  |  |  | Invention product 1 | Comparative product 1 | Invention product 2 | Comparative product 2 |
|---|---|---|---|---|---|---|
|  | Composition (wt %) |  |  |  |  |  |
| Component (a) | Glyphosate.diammonium salt |  | — | — | — | — |
|  | Glyphosate.monoisopropylamine salt |  | 57.0 | 57.0 | 51.0 | 51.0 |
|  | Glufosinate.monoammonium salt |  | — | — | — | — |
| Component (b) | Compound (1) |  | — | — | — | — |
|  | Compound (2) |  | — | — | — | — |
|  | Compound (3) |  | 7.0 | 3.0 | 8.0 | 8.0 |
|  | Compound (4) |  | — | — | — | — |
| Component (c) | Compound (5) |  | 3.0 | — | — | — |
|  | Compound (6) |  | — | — | — | — |
|  | Compound (7) |  | — | — | 2.0 | — |
| Component (d) | Potassium oxalate |  | — | — | 3.5 | 3.5 |
|  | EDTA.4Na |  | — | — | — | — |
|  | Ammonium sulfate |  | — | — | — | — |
|  | Ammonium phosphate |  | — | — | — | — |
| Others | POE(7) secondary $C_{12-13}$ alcohol |  | — | — | — | — |
|  | POE(9) palm fatty acid glycerol ester |  | — | — | — | — |
|  | water |  | 33.0 | 40.0 | 35.5 | 37.5 |
| Results of evaluations | Condition of composition |  | one solution transparent | white turbidity separated into two phases | one solution transparent | separated into two phases |
|  | Stability | −5° C. | stable | could not be evaluated | stable | could not be evaluated |
|  |  | 60° C. | stable | could not be evaluated | stable | could not be evaluated |

Note)
In the Table, "POE" is an abbreviation for polyoxyethylene, and the figures in parentheses present behind the POE stand for the average numbers of oxyethylene groups per one molecule (the same will be applied to the following Tables).

TABLE 3

|  |  |  | Invention product 3 | Comparative product 3 | Invention product 4 | Comparative product 4 |
|---|---|---|---|---|---|---|
|  | Composition (wt %) |  |  |  |  |  |
| Component (a) | Glyphosate.diammonium salt |  | 36.0 | 36.0 | — | — |
|  | Glyphosate.monoisopropylamine salt |  | — | — | — | — |
|  | Glufosinate.monoammonium salt |  | — | — | 43.0 | 43.0 |
| Component (b) | Compound (1) |  | — | — | 5.2 | 5.2 |
|  | Compound (2) |  | — | — | — | — |
|  | Compound (3) |  | — | — | — | — |
|  | Compound (4) |  | 5.2 | 5.2 | — | — |
| Component (c) | Compound (5) |  | — | — | — | — |
|  | Compound (6) |  | — | — | 3.5 | — |
|  | Compound (7) |  | 3.5 | — | — | — |
| Component (d) | Potassium oxalate |  | — | — | — | — |
|  | EDTA.4Na |  | — | — | — | — |
|  | Ammonium sulfate |  | 8.0 | 8.0 | — | — |
|  | Ammonium phosphate |  | — | — | 8.0 | 8.0 |
| Others | POE(7) secondary $C_{12-13}$ alcohol |  | — | — | — | — |
|  | POE(9) palm fatty acid glycerol ester |  | — | — | — | — |
|  | water |  | 47.3 | 50.8 | 40.3 | 43.8 |
| Results of evaluations | Condition of composition |  | one solution transparent | separated into two phases sedimentation | one solution transparent | separated into two phases sedimentation |
|  | Stability | −5° C. | stable | could not be evaluated | stable | could not be evaluated |
|  |  | 60° C. | stable | could not be evaluated | stable | could not be evaluated |

TABLE 4

|  |  | Invention product 5 | Comparative product 5 | Invention product 6 | Comparative product 6 |
|---|---|---|---|---|---|
|  | Composition (wt %) |  |  |  |  |
| Component (a) | Glyphosate.diammonium salt | 42.0 | 42.0 | — | — |
|  | Glyphosate.monoisopropylamine | — | — | 54.0 | 54.0 |

TABLE 4-continued

|  |  | Invention product 5 | Comparative product 5 | Invention product 6 | Comparative product 6 |
|---|---|---|---|---|---|
|  | salt |  |  |  |  |
|  | Glufosinate.monoammonium salt | — | — | — | — |
| Component (b) | Compound (1) | — | — | — | — |
|  | Compound (2) | — | — | 10.0 | 7.5 |
|  | Compound (3) | 5.0 | 2.5 | — | — |
|  | Compound (4) | — | — | — | — |
| Component (c) | Compound (5) | 2.0 | — | 2.8 | — |
|  | Compound (6) | — | — | — | — |
|  | Compound (7) | — | — | — | — |
| Component (d) | Potassium oxalate | — | — | — | — |
|  | EDTA.4Na | — | — | — | — |
|  | Ammonium sulfate | — | — | — | — |
|  | Ammonium phosphate | — | — | — | — |
| Others | POE(7) secondary $C_{12-13}$ alcohol | 3.0 | 3.0 | — | — |
|  | POE(9) palm fatty acid glycerol ester | — | — | — | — |
|  | water | 48.0 | 52.5 | 33.2 | 38.5 |
| Results of evaluations | Condition of composition | one solution transparent | separated into two phases | one solution transparent | white turbidity separated into two phases |
|  | Stability −5° C. | stable | could not be evaluated | stable | could not be evaluated |
|  | 60° C. | stable | could not be evaluated | stable | could not be evaluated |

TABLE 5

|  |  | Invention product 7 | Comparative product 7 | Invention product 8 | Comparative product 8 |
|---|---|---|---|---|---|
|  | Composition (wt %) |  |  |  |  |
| Component (a) | Glyphosate.diammonium salt | 42.0 | 42.0 | — | — |
|  | Glyphosate.monoisopropylamine salt | — | — | 51.0 | 51.0 |
|  | Glufosinate.monoammonium salt | — | — | — | — |
| Component (b) | Compound (1) | — | — | 6.0 | 6.0 |
|  | Compound (2) | — | — | — | — |
|  | Compound (3) | 7.0 | 3.0 | — | — |
|  | Compound (4) | — | — | — | — |
| Component (c) | Compound (5) | — | — | — | — |
|  | Compound (6) | 2.0 | — | — | — |
|  | Compound (7) | — | — | 2.0 | — |
| Component (d) | Potassium oxalate | — | — | — | — |
|  | EDTA.4Na | 4.0 | 4.0 | — | — |
|  | Ammonium sulfate | — | — | — | — |
|  | Ammonium phosphate | — | — | — | — |
| Others | POE(7) secondary $C_{12-13}$ alcohol | — | — | — | — |
|  | POE(9) palm fatty acid glycerol ester | — | — | 3.0 | 3.0 |
|  | water | 45.0 | 51.0 | 38.0 | 40.0 |
| Results of evaluations | Condition of composition | one solution transparent | white turbidity separated into two phases | one solution transparent | separated into two phases sedimentation |
|  | Stability −5° C. | stable | could not be evaluated | stable | could not be evaluated |
|  | 60° C. | stable | could not be evaluated | stable | could not be evaluated |

TABLE 6

|  |  | Invention product 9 | Comparative product 9 | Invention product 10 | Comparative product 10 |
|---|---|---|---|---|---|
|  | Composition (wt %) |  |  |  |  |
| Component (a) | Glyphosate.diammonium salt | — | — | — | — |
|  | Glyphosate.monoisopropylamine salt | — | — | 50.0 | 50.0 |
|  | Glufosinate.monoammonium salt | 45.0 | 45.0 | — | — |
| Component (b) | Compound (1) | — | — | — | — |
|  | Compound (2) | — | — | — | — |
|  | Compound (3) | 5.2 | 3.0 | — | — |
|  | Compound (4) | — | — | 6.0 | 3.0 |

TABLE 6-continued

|  |  |  | Invention product 9 | Comparative product 9 | Invention product 10 | Comparative product 10 |
|---|---|---|---|---|---|---|
| Component (c) | Compound (5) |  | 3.5 | — | 3.0 | — |
|  | Compound (6) |  | — | — | — | — |
|  | Compound (7) |  | — | — | — | — |
| Component (d) | Potassium oxalate |  | — | — | — | — |
|  | EDTA.4Na |  | — | — | — | — |
|  | Ammonium sulfate |  | — | — | — | — |
|  | Ammonium phosphate |  | 8.0 | 8.0 | — | — |
| Others | POE(7) secondary $C_{12-13}$ alcohol |  | — | — | 2.0 | 2.0 |
|  | POE(9) palm fatty acid glycerol ester |  | — | — | — | — |
|  | water |  | 38.3 | 44.0 | 39.0 | 45.0 |
| Results of evaluations | Condition of composition |  | one solution transparent | separated into two phases | one solution transparent | separated into two phases sedimentation |
|  | Stability | −5° C. | stable | could not be evaluated | stable | could not be evaluated |
|  |  | 60° C. | stable | could not be evaluated | stable | could not be evaluated |

TABLE 7

|  |  |  | Invention product 11 | Comparative product 11 | Invention product 12 | Comparative product 12 |
|---|---|---|---|---|---|---|
|  | Composition (wt %) |  |  |  |  |  |
| Component (a) | Glyphosate.diammonium salt |  | 40.0 | 40.0 | — | — |
|  | Glyphosate.monoisopropylamine salt |  | — | — | — | — |
|  | Glufosinate.monoammonium salt |  | — | — | 43.0 | 43.0 |
| Component (b) | Compound (1) |  | — | — | — | — |
|  | Compound (2) |  | 5.0 | 2.5 | — | — |
|  | Compound (3) |  | — | — | — | — |
|  | Compound (4) |  | — | — | 6.0 | 3.0 |
| Component (c) | Compound (5) |  | — | — | — | — |
|  | Compound (6) |  | — | — | 3.0 | — |
|  | Compound (7) |  | 2.5 | — | — | — |
| Component (d) | Potassium oxalate |  | — | — | — | — |
|  | EDTA.4Na |  | — | — | — | — |
|  | Ammonium sulfate |  | — | — | 10.0 | 10.0 |
|  | Ammonium phosphate |  | — | — | — | — |
| Others | POE(7) secondary $C_{12-13}$ alcohol |  | 2.0 | 2.0 | — | — |
|  | POE(9) palm fatty acid glycerol ester |  | — | — | — | — |
|  | water |  | 50.5 | 55.5 | 38.0 | 44.0 |
| Results of evaluations | Condition of composition |  | one solution transparent | separated into two phases sedimentation | one solution transparent | white turbidity separated into two phases |
|  | Stability | −5° C. | stable | could not be evaluated | stable | could not be evaluated |
|  |  | 60° C. | stable | could not be evaluated | stable | could not be evaluated |

TABLE 8

|  |  | Invention product 13 | Invention product 14 | Invention product 15 | Invention product 16 |
|---|---|---|---|---|---|
|  | Composition (wt %) |  |  |  |  |
| Component (b) | Compound (1) | — | — | — | 18.8 |
|  | Compound (2) | — | — | 78 | — |
|  | Compound (3) | 50 | — | — | — |
|  | Compound (4) | — | 18.8 | — | — |
| Component (c) | Compound (5) | 10 | — | — | — |
|  | Compound (6) | — | — | 22 | — |
|  | Compound (7) | — | 12.8 | — | 12.8 |
| Component (d) | Potassium oxalate | — | — | — | — |
|  | EDTA.4Na | — | — | — | — |
|  | Ammonium sulfate | — | 28.5 | — | — |
|  | Ammonium phosphate | — | — | — | 28.5 |
| Others | POE(7) secondary $C_{12-13}$ alcohol | 30 | — | — | — |
|  | POE(9) palm fatty acid glycerol ester | — | — | — | — |
|  | water | 10 | 39.9 | — | 39.9 |

TABLE 8-continued

|  |  |  | Invention product 13 | Invention product 14 | Invention product 15 | Invention product 16 |
|---|---|---|---|---|---|---|
| Results of evaluations | Condition of composition | | one solution transparent | one solution transparent | one solution transparent | one solution transparent |
| | Stability | −5° C. | stable | stable | stable | stable |
| | | 60° C. | stable | stable | stable | stable |

We claim:

1. An aqueous liquid agricultural composition comprising 25 to 85 weight percent of (a) a water-soluble agricultural chemical which is an organo-phosphorus herbicide, 0.35 to 30 weight percent of (b) at least one member selected from the group consisting of compounds represented by the following formula (I), and (c) at least one member selected from the group consisting of acid salts of compounds represented by the following formula (II) and compounds represented by the following formula (III), wherein the weight ratio of component (b) to component (c) is from 9:1 to 1:9:

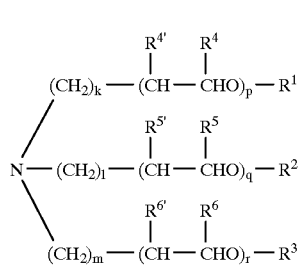
(I)

wherein $R^1$, $R^2$ and $R^3$ may be the same or different from one another and each independently represents a hydrogen atom, a linear or branched alkyl or alkenyl group having 5 to 29 carbon atoms, a group represented by the formula:

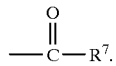

wherein $R^7$ represents a linear or branched alkyl or alkenyl group having 5 to 29 carbon atoms, or a group represented by the formula:

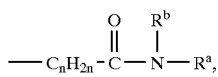

wherein $R^a$ represents a linear or branched alkyl or alkenyl group having 5 to 29 carbon atoms, $R^b$ represents a hydrogen atom, a linear or branched alkyl group having 1 to 30 carbon atoms or a linear or branched alkenyl group having 2 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30:

$R^4$ and $R^{4'}$ are both hydrogen atoms or one of them is a hydrogen atom and the other is a methyl group or an ethyl group, with the proviso that when two or more groups each represented by the formula:

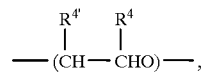

wherein $R^4$ and $R^{4'}$ are each as defined above, are contained therein, these groups may be the same or different from one another;

$R^5$ and $R^{5'}$ are both hydrogen atoms or one of them is a hydrogen atom and the other is a methyl group or an ethyl group, with the proviso that when two or more groups each represented by the formula:

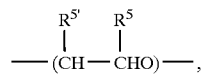

wherein $R^5$ and $R^{5'}$ are each as defined above, are contained therein, these groups may be the same or different from one another;

$R^6$ and $R^{6'}$ are both hydrogen atoms or one of them is a hydrogen atom and the other is a methyl group or an ethyl group, with the proviso that when two or more groups, each represented by the formula:

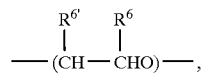

wherein $R^6$ and $R^{6'}$ are each as defined above, are contained therein, these groups may be the same or different from one another; and k, l and m may be the same or different from one another and are each independently a number of 0 to 6,

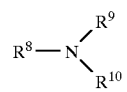
(II)

wherein, $R^8$ represents a linear or branched, or cyclic, alkyl or alkenyl group having 4 to 18 carbon atoms; and $R^9$ and $R^{10}$ may be the same or different from each other and are each independently a hydrogen atom, a methyl group or an ethyl group, and

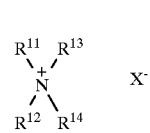
(III)

wherein $R^{11}$ represents a linear or branched alkyl or alkenyl group having 4 to 18 carbon atoms; $R^{12}$ represents a linear or branched alkyl group having 1 to 18 carbon atoms or a linear or branched alkenyl group having 2 to 18 carbon atoms; $R^{13}$ and $R^{14}$ may be the same or different from each other and are each independently a methyl group, an ethyl group or a benzyl group; and $X^-$ is a counter anion.

2. The aqueous liquid agricultural composition according to claim 1, which further comprises at least one member selected from the group consisting of chelating agents and water-soluble inorganic salts.

3. The aqueous liquid agricultural composition according to claim 1, wherein component (b) is at least one member selected from the group consisting of quaternary ammonium salts of the compounds represented by the above formula (I).

4. The aqueous liquid agricultural composition according to claim 1, wherein component (c) is at least one member selected from the group consisting of acid salts of the compounds represented by the above formula (II).

5. The aqueous liquid agricultural composition according to claim 2, wherein component (c) is at least one member selected from the group consisting of the compounds represented by the above formula (III).

6. A method for converting an aqueous liquid agricultural composition (1) comprising 25 to 85 weight percent of (a) water-soluble herbicidal chemical and 0.35 to 30 weight percent of (b) at least one member selected from the group consisting of compounds represented by the following formula (I) into a stable liquid, which comprises adding (c) at least one member selected from the group consisting of acid salts of compounds represented by the following formula (II) and compounds represented by the following formula (III); wherein the weight ratio of component (b) to component (c) is from 9:1 to 1:9, to the composition (1):

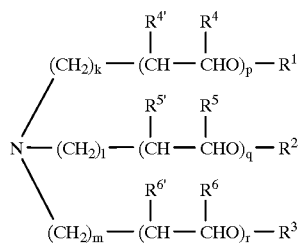

(I)

wherein $R^1$, $R^2$ and $R^3$ may be the same or different from one another and each independently represents a hydrogen atom, a linear or branched alkyl or alkenyl group having 5 to 29 carbon atoms, a group represented by the formula:

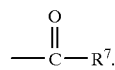

wherein $R^7$ represents a linear or branched alkyl or alkenyl group having 5 to 29 carbon atoms, or a group represented by the formula:

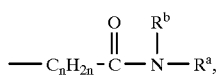

wherein $R^a$ represents a linear or branched alkyl or alkenyl group having 5 to 29 carbon atoms, $R^b$ represents a hydrogen atom, a linear or branched alkyl group having 1 to 30 carbon atoms or a linear or branched alkenyl ground having 2 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30;

$R^4$ and $R^{4'}$ are both hydrogen atoms or one of them is a hydrogen atom and the other is a methyl group or an ethyl group, with the proviso that when two or more groups each represented by the formula:

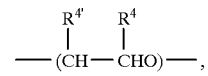

wherein $R^4$ and $R^{4'}$ are each as defined above, are contained therein, these groups may be the same or different from one another;

$R^5$ and $R^{5'}$ are both hydrogen atoms or one of them is a hydrogen atom and the other is a methyl group or an ethyl group, with the proviso that when two or more groups each represented by the formula:

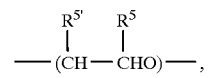

wherein $R^5$ and $R^{5'}$ are each as defined above, are contained therein, these groups may be the same or different from one another;

$R^6$ and $R^{6'}$ are both hydrogen atoms or one of them is a hydrogen atom and the other is a methyl group or an ethyl group, with the proviso that when two or more groups each represented by the formula:

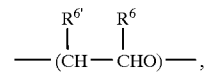

wherein $R^6$ and $R^{6'}$ are each as defined above, are contained therein, these groups may be the same or different from one another; and k, l and m may be the same or different from one another and are each independently a number of 0 to 6,

(II)

wherein, $R^8$ represents a linear or branched, or cyclic, alkyl or alkenyl group having 4 to 18 carbon atoms; and $R^9$ and $R^{10}$ may be the same or different from each other and are each independently a hydrogen atom, a methyl group or an ethyl group, and

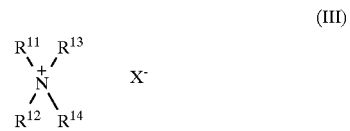

(III)

wherein $R^{11}$ represents a linear or branched alkyl or alkenyl group having 4 to 18 carbon atoms; $R^{12}$ represents a linear or branched alkyl group having 1 to 18 carbon atoms or a linear or branched alkenyl group having 2 to 18 carbon atoms; $R^{13}$ and $R^{14}$ may be the same or different from each other and are each independently a methyl group, an ethyl group or a benzyl group; and $X^-$ is a counter anion.

7. The method for converting a composition (1) into a stable liquid according to claim 6, wherein the composition (1) further comprises at least one member selected from the group consisting of chelating agents and water-soluble inorganic salts.

8. An adjuvant composition for water-soluble herbicidal chemicals comprising (b) 0.35 to 30 weight percent of at least one member selected from the group consisting of compounds represented by the following formula (I), and (c) at least one member selected from the group consisting of acid salts of compounds represented by the following formula (II) and compounds represented by the following formula (III), wherein the weight ratio of component (b) to component (c) is from 9:1 to 1:9:

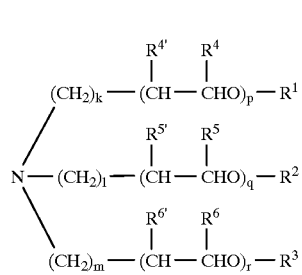
(I)

wherein $R^1$, $R^2$ and $R^3$ may be the same or different from one another and each independently represents a hydrogen atom, a linear or branched alkyl or alkenyl group having 5 to 29 carbon atoms, a group represented by the formula:

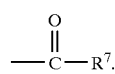

wherein $R^7$ represents a linear or branched alkyl or alkenyl group having 5 to 29 carbon atoms, or a group represented by the formula:

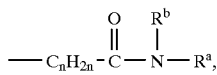

wherein $R^a$ represents a linear or branched alkyl or alkenyl group having 5 to 29 carbon atoms, $R^b$ represents a hydrogen atom, a linear or branched alkyl group having 1 to 30 carbon atoms or a linear or branched alkenyl group having 2 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30;

$R^4$ and $R^{4'}$ are both hydrogen atoms or one of them is a hydrogen atom and the other is a methyl group or an ethyl group, with the proviso that when two or more groups each represented by the formula:

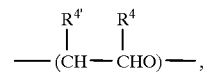

wherein $R^4$ and $R^{4'}$ are each as defined above, are contained therein, these groups may be the same or different from one another;

$R^5$ and $R^{5'}$ are both hydrogen atoms or one of them is a hydrogen atom and the other is a methyl group or an ethyl group, with the proviso that when two or more groups each represented by the formula:

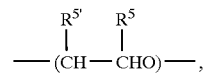

wherein $R^5$ and $R^{5'}$ are each as defined above, are contained therein, these groups may be the same or different from one another;

$R^6$ and $R^{6'}$ are both hydrogen atoms or one of them is a hydrogen atom and the other is a methyl group or an ethyl group, with the proviso that when two or more groups each represented by the formula:

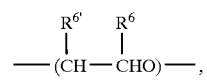

wherein $R^6$ and $R^{6'}$ are each as defined above, are contained therein, these groups may be the same or different from one another; and k, l and m may be the same or different from one another and are each independently a number of 0 to 6,

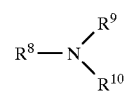
(II)

wherein, $R^8$ represents a linear or branched, or cyclic, alkyl or alkenyl group having 4 to 18 carbon atoms; and $R^9$ and $R^{10}$ may be the same or different from each other and are each independently a hydrogen atom, a methyl group or an ethyl group, and

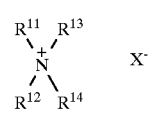
(III)

wherein $R^{11}$ represents a linear or branched alkyl or alkenyl group having 4 to 18 carbon atoms; $R^{12}$ represents a linear or branched alkyl group having 1 to 18 carbon atoms or a linear or branched alkenyl group having 2 to 18 carbon atoms; $R^{13}$ and $R^{14}$ may be the same or different from each other and are each independently a methyl group, an ethyl group or a benzyl group; and $X^-$ is a counter anion; and an agricultural chemical present in an amount of 25 to 85 weight percent based on the total composition.

9. The adjuvant composition for agricultural chemicals according to claim 8, which further comprises at least one member selected from the group consisting of chelating agents and water-soluble inorganic salts.

10. An aqueous liquid agricultural composition comprising 25 to 85 weight percent of (a) a water-soluble herbicidal chemical, 0.35 to 30 weight percent of (b) at least one member selected from the group consisting of compounds represented by the following formula (I), and (c) at least one member selected from the group consisting of acid salts of compounds represented by the following formula (II) and compounds represented by the following formula (III), wherein the weight ratio of component (b) to component (c) is from 9:1 to 1:9:

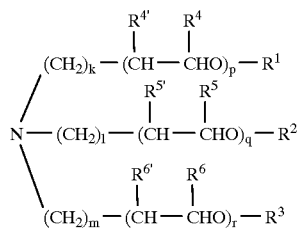 (I)

wherein $R^1$, $R^2$ and $R^3$ may be the same or different from one another and each independently represents a hydrogen atom, a linear or branched alkyl or alkenyl group having 5 to 29 carbon atoms, a group represented by the formula:

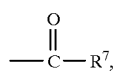

wherein $R^7$ represents a linear or branched alkyl or alkenyl group having 5 to 29 carbon atoms, or a group represented by the formula:

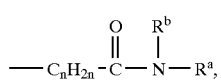

wherein $R^a$ represents a linear or branched alkyl or alkenyl group having 5 to 29 carbon atoms, $R^b$ represents a hydrogen atom, a linear or branched alkyl group having 1 to 30 carbon atoms or a linear or branched alkenyl group having 2 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30;

$R^4$ and $R^{4'}$ are both hydrogen atoms or one of them is a hydrogen atom and the other is a methyl group or an ethyl group, with the proviso that when two or more groups each represented by the formula:

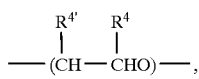

wherein $R^4$ and $R^{4'}$ are each as defined above, are contained therein, these groups may be the same or different from one another;

$R^5$ and $R^{5'}$ are both hydrogen atoms or one of them is a hydrogen atom and the other is a methyl group or an ethyl group, with the proviso that when two or more groups each represented by the formula:

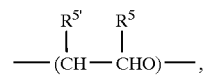

wherein $R^5$ and $R^{5'}$ are each as defined above, are contained therein, these groups may be the same or different from one another;

$R^6$ and $R^{6'}$ are both hydrogen atoms or one of them is a hydrogen atom and the other is a methyl group or an ethyl group, with the proviso that when two or more groups each represented by the formula:

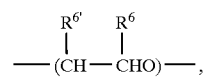

wherein $R^6$ and $R^{6'}$ are each as defined above, are contained therein, these groups may be the same or different from one another; and k, l and m may be the tame or different from one another and are each independently a number of 0 to 6,

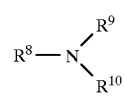 (II)

wherein, R8 represents a linear or branched, or cyclic, alkyl or alkenyl group having 4 to 18 carbon atoms; and $R^9$ and $R^{10}$ may be the same or different from each other and are each independently a hydrogen atom, a methyl group or an ethyl group, and

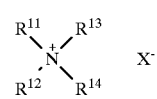 (III)

wherein $R^{11}$ represents a linear or branched alkyl or alkenyl group having 4 to 18 carbon atoms; $R^{12}$ represents a linear or branched alkyl group having 1 to 18 carbon atoms or a linear or branched alkenyl group having 2 to 18 carbon atoms; $R^{13}$ and $R^{14}$ may be the same or different from each other and are each independently a methyl group, an ethyl group or a benzyl group; and $X^-$ is a counter anion.

* * * * *